United States Patent [19]
Jonjic

[11] Patent Number: 5,993,208
[45] Date of Patent: *Nov. 30, 1999

[54] METHOD FOR PRECISELY FIXING A UNIFORM PREDETERMINED THICKNESS OF A PALATAL PROSTHESES

[76] Inventor: Leo Jonjic, C.M. Tita 31, 51414, Ika-Icici, Croatia

[*] Notice: This patent is subject to a terminal disclaimer.

[21] Appl. No.: 08/877,180

[22] Filed: Jun. 17, 1997

Related U.S. Application Data

[63] Continuation-in-part of application No. 08/562,378, Nov. 24, 1995.

[30] Foreign Application Priority Data

Jun. 5, 1995 [HR] Croatia .................................. P950318A

[51] Int. Cl.$^6$ ....................................................... A61C 3/00
[52] U.S. Cl. ................................. 433/50; 433/34; 433/56; 433/75
[58] Field of Search ........................... 433/6, 34, 50 OR, 433/49, 53, 56, 75

[56] References Cited

U.S. PATENT DOCUMENTS

| | | | |
|---|---|---|---|
| 1,753,965 | 4/1930 | Ralph | 433/56 |
| 2,724,899 | 11/1955 | Stoll | 433/75 |
| 3,600,752 | 8/1971 | Kopp | 433/34 |
| 3,760,504 | 9/1973 | Ljubarsky et al. | 433/50 |
| 4,184,255 | 1/1980 | Gordon | 433/6 |
| 4,290,754 | 9/1981 | Edwardson | 433/56 |
| 4,484,894 | 11/1984 | Masuhara et al. | 433/168.1 |
| 4,510,556 | 4/1985 | Zeinigher | 433/56 |
| 4,762,490 | 8/1988 | Ludwigs | 433/56 |
| 5,257,932 | 11/1993 | Leinfelder et al. | 433/56 |

Primary Examiner—John J. Wilson

[57] ABSTRACT

The instant invention provides a method and an apparatus for forming a palatal plate prosthesis of a substantially precise, predetermined uniform thickness. The apparatus includes: a base having three leveling supports; a first component attachable to the base in one of a plurality of positions, for fixing a first casting which includes a first impression of the palate of a patient; wherein the first impression is fixed by the first component, so as to generally lie in a first horizontal plane; a second component for fixing a second casting which includes a second impression formed by applying casting material over the substantial entirety of the first impression; wherein the second impression is movably fixed by the second component, so as to generally lie in a second horizontal plane which is generally parallel to, and equidistant from, the first horizontal plane; and, a third component for enabling vertical displacement of the first impression from the second impression substantially precisely equal to the predetermined uniform thickness. The third component further includes: a shaft having at least one retention element at the lowest end thereof, for fixing the second casting thereto; and, a shaft elevator for vertically, non-rotationally, displacing the shaft. The apparatus further includes a fourth component attached to the shaft elevator for supporting the third component; a stop located between the shaft elevator and the fourth component for stopping downward vertical travel of the shaft elevator; a spacer having a thickness substantially equal to the substantially precise, predetermined uniform thickness, insertable between the lowest most end of the shaft elevator and the stop; and, at least one generally vertical post for fixing the fourth component to the base.

7 Claims, 3 Drawing Sheets

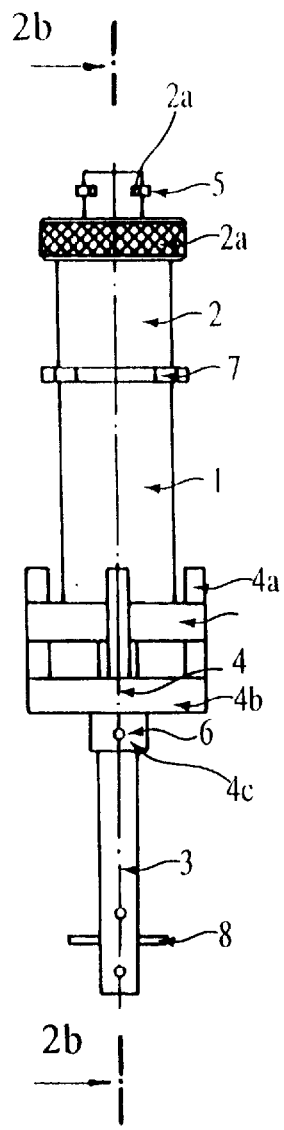
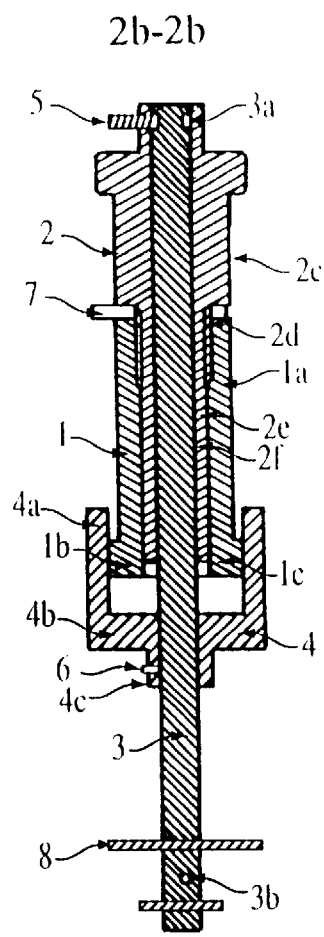
FIG. 2A  FIG. 2B
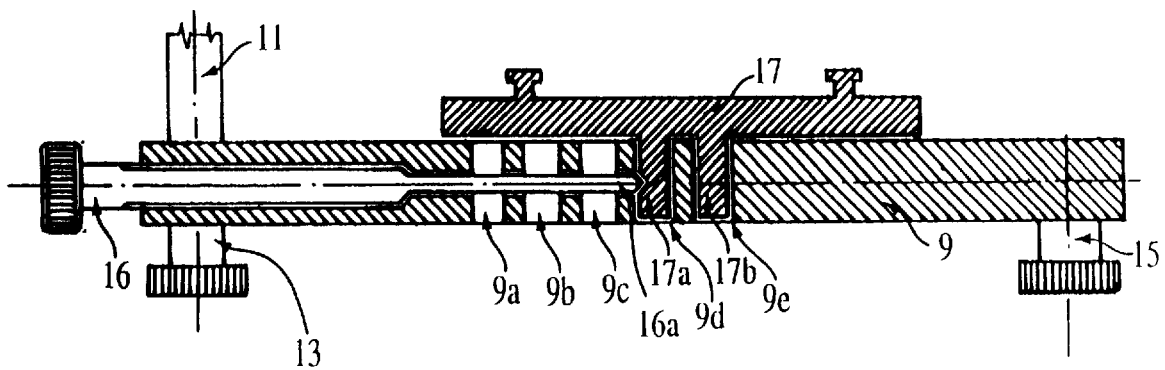
FIG. 3

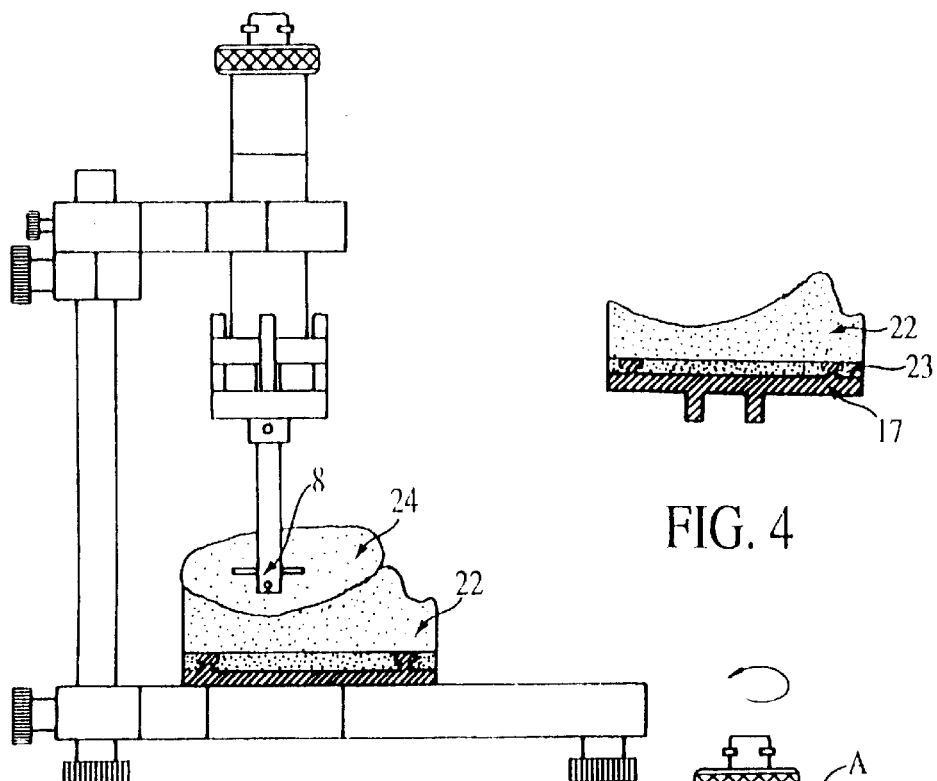
FIG. 4
FIG. 5
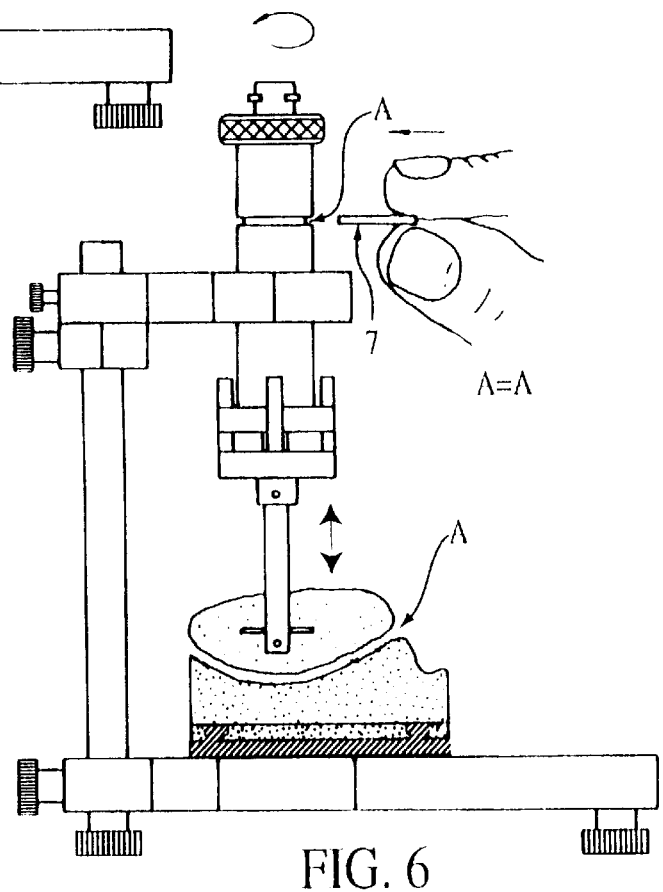
FIG. 6

METHOD FOR PRECISELY FIXING A UNIFORM PREDETERMINED THICKNESS OF A PALATAL PROSTHESES

RELATED APPLICATION DATA

This is a continuation-in-part of application Ser. No. 08/562,378, filed Nov. 24, 1995, presently pending.

BACKGROUND OF THE INVENTION

The instant invention is broadly related to the dentistry specialty of prosthodontics. More specifically the invention is related to an apparatus and method for preparing a palatal plate prosthesis. Still more specifically, the invention is related to an apparatus and method for preparing a palatal plate prosthesis having a predetermined uniform thickness. Still even more specifically, the invention is related to an apparatus and method for preparing a palatal plate prosthesis having a predetermined uniform thickness sufficient for eliminating the problem of hissing typically associated with a prosthesis having a non-uniform and/or non-predetermined thickness.

As noted in *Encaria96 Encyclopedia*, dentistry, a health profession concerned with the prevention, diagnosis, and treatment of disorders of the teeth and adjacent tissues of the head, neck, and mouth. A dentist is a person possessing the education, experience, and legal qualifications required to practice dentistry or any of its phases. The practice of dentistry includes cleaning, filling, and extracting teeth, treating diseased gum tissues, correcting irregularities in tooth alignment, performing surgical operations on the mouth or jaw, and constructing and fitting artificial teeth or dentures.

Disorders in the mouth may cause diseases of other parts of the body; conversely, the teeth and their supporting structures are affected by abnormal conditions in distant parts of the body. Because dental structures generally cannot repair themselves, care of the mouth represents a unique health problem for which dentistry uses its own procedures and techniques, as well as those of medicine, in order to prevent local complications as well as ill effects throughout the body.

Most dentists are general practitioners in all phases of dentistry. Periodic examinations, including the use of X rays and special instruments and tests, are required in order to detect disorders in an early stage. Encrustations of calctiltis (tartar), which consists of mineralized bacterial plaque, products of bacterial metabolism, salivary mucus, and food residue, should be removed from the teeth at least once a year. Cavities in the teeth are filled with any of various appropriate materials. Irregularities of alignment are corrected. Teeth badly broken down may be rebuilt, or the dental pulp of infected teeth may require removal. Teeth incapable of being restored must be extracted, and missing teeth need to be replaced by artificial ones.

Dentistry is subdivided into specialized fields, although the general practitioner may undertake as many of them as his or her interest and capabilities permit. The specialty of interest here is prosthodontics. Prosthodontics is the phase of dental science which deals with the various methods of providing artificial substitutes, or dentures, for missing teeth, the replacement of which ensures the even distribution of the forces involved in chewing and thus prevents the loss of other teeth as a result of undue stress. The nature of the restoration depends on the health of the remaining teeth and supporting structures. If feasible, a fixed bridge is used to replace missing teeth. This type of replacement is accomplished by constructing crowns, which cover all or a large part of the adjacent teeth, and then by attaching the artificial teeth to the crowns. A fixed bridge made of gold covered with porcelain or acrylic (a plastic material) is lifelike and cannot be readily removed. If sufficient adjacent teeth do not remain to support a fixed bridge, then a removable partial denture is constructed. This type of prosthetic device is usually secured by clasps, which embrace several of the remaining teeth. The clasps may be made of gold or of a cobalt-steel alloy This type of appliance must be removed frequently to be cleaned. When all teeth must be replaced, a full denture is made. The retention of this type of denture depends on the firmnness of the underlying tissues and the adhesion provided by the saliva in the mouth. Full dentures are usually made of acrylic, reinforced occasionally with metal. Prosthodontists also replace portions of the oral cavity that are missing because of malformations or deficiencies.

Various prior art inventions have addressed various problems which arise in the specialty of prosthodontics.

U.S. Pat. No. 5,195,513, to Sinko, et al, teaches a prosthesis for protecting the palate of a small infant from injury by airway or other tubes required to be maintained in the throat of an infant patient for extended periods, which comprises a thin mass of injection molded, soft resiliently deformable plastic having an upper surface contoured to conform to a normal palate of a healthy infant of approximately the same size as the patient. The plastic mass incorporates an integral, downwardly opening passage for an air way tube, thus disposing the plastic mass between the tube and the palate of the infant patient.

U.S. Pat. No. 4,112,934 to Rizk teaches an apparatus for preventing damage to the alveolar ridge and to any teeth, crowns, or dental prosthesis protruding therefrom during the administration of anesthetic and during insertion of rigid instruments into a patient's mouth. A protector is constructed with a removable handle and is arranged to sit astride the maxillary alveolar ridge. The protector is generally "U"-shaped in cross-section, curved to conform to the arc of the maxillary alveolar ridge, and the arms of the "U" are shaped to be located, respectively, within the anterior maxillary labial vestibule and to bear against the hard palate. The depth of the protector prevents the interior thereof from contacting either the maxillary alveolar ridge itself or any protuberances therefrom. When the protector is in place astride the maxillary alveolar ridge, its shape and size diverts the force of any blow received by the protector or any pressure applied to it, away from the maxillary alveolar ridge and toward the maxillary labial vestibule and the hard palate. The handle member which is removably fixed to the protector, is usable in maintaining the protector in position and also usable as an aid in opening a patient's mouth by applying traction thereto during intubation.

U.S. Pat. No. 4,175,322 to Tureaud, discloses for both maxillary and mandibular prostheses of the type having a hard base structure formed of acrylic plastic into which prosthetic teeth are set, the hard base structure fused to a deflectable tray layer of thermo plastic material which is deflectable when warm to adapt the denture to the general contours of the maillary or mandibular ridges, a subsequent coating of autopolymerizing acrylic plastic being applied to the tray providing precise fitting of the denture to the oral contours ofthe wearer and stabilizing the soft deflectable tray in its newly achieved configuration. The hard base structure disclosed provides a fight bond to the prosthetic teeth and holds them securely in position in the occlusal plane but features a segmentation which allows lateral adjustment in the relative position of the posterior prosthetic teeth in each segment with respect to the teeth in the other segments to thus provide a capability for adjusting the prosthetic teeth to the maxillary or mandibular residual ridges. The segmentation in the preferred embodiment is provided by extending a thin juncture of deflectable material between two anterior teeth, i.e., the central incisors, to allow each half of the denture to be laterally shifted with respect to the other during fitting of the denture. Also disclosed, in the maxillary denture, is a pleat formed in that portion of the deflectable tray layer forming the palatal vault which serves to accommodate any shifing in position of the respective hard base structure segments. An alternate embodiment discloses the segmentation of the hard base structure into three segments, a first segment into which are mounted the anterior prosthetic teeth and two posterior teeth carrying segments. In the method of fitting the denture, the segments are laterally adjusted during fitting operation with respect to each other to align the prosthetic teeth with maxillary and mandibular ridges. The resulting denture may be either directly used as a prosthesis or used as a model in constructing a final prosthesis.

U.S. Pat. No. 5,584,694 Forsmalm, et al, teaches a method which increases the precision of the components in an impression system for dental prosthesis of the type permanently anchored in the jaw by at least one securing elements implanted in the jawbone. Each of the securing elements is provided with a distance member whose upper part protrudes above the palatal arch and on which the finished dental bridge/dental prosthesis is then anchored via a so-called gold cylinder. The system includes impression components in the form of impression tops and distance dummies with continuous guide holes and stop members for a guide pin which, during fixing of the components, is guided through the respective guide hole and engages with the stop members of the respective impression component. That part of the guide pin which interacts with the stop members of the guide holes of the respective impression component has a conical stop surface, while the stop members form plane surfaces and guide edges. By such a design of the guide pin, the components are centered and the precision is improved in existing impression systems.

U.S. Pat. No. 4,886,453 to Ludwigs, teaches a module for an apparatus (system) to produce upper and lower jaw filil prostheses which has an instrument holder (66) consisting of a baseplate (3), supporting two upright pillars (4) and a tilting arm (6) that can be pivoted on a horizontal axis (5) around the pillars (4), on which auxiliary instruments developed for individual work processes can be adapted. In terms of auxiliary instruments, the module has an infinitely adjustable levelling table (9) set on the baseplate (3), a lower jaw alignment key (10), an impression or mounting plate (7, 8), an upper jaw model alignment key, a domed setting aid for correct setting of teeth on the lower jaw fill prosthesis and a domed setting aid with dummy tooth for correct setting of the 1st right and left tooth on lower jaw full prostheses, which can be attached to the instrument holder (66) in a secure position and interchanged.

U.S. Pat. No. 4,869,669 to Grubbs, teaches an oral chock which exerts uniformly axial forces on dental prostheses to seat the prosthesis. The chock is preferably shaped like the dental arch, and wedge-shaped to align the surfaces of the chock with the occlusal surfaces of the teeth. The chock is large enough to receive the entire dental arch, so that one or a plurality of prostheses of any size or extent can be seated. The chock may be scored for separation into partial chocks, and the central posterior portion may be removed for palatal and lingual relief The chock is formed of expanded plastic material having a frangible cellular structure for deformation of the chock so that the chock will exert uniformly distributed forces. Though deformable, the material has sufficient strength to seat the prostheses.

U.S. Pat. No. 5,472,344 to Binder, et al, teaches an expansion screw for tooth adjustment having two expansion screw body members each embeddable in a plastic palate plate, these body members being provided with retention grooves for anchoring in the plastic of these palate plates, also having a threaded spindle and two guide pins, wherein the threaded spindle has spindle sections with opposite threads on either side of a central section, these spindle sections engaging in corresponding threaded bores of the expansion screw body members, and wherein the latter have guide openings for the passage of the guide pins extending parallel to the threaded spindle. In order to reduce the size of the two expansion screw body members, the latter are of a hat-shaped design in the side view and provided at their central regions with retention grooves and, in addition, at their facing inner end faces with recesses for accommodating the central section of the threaded spindle, these recesses being designed such that these end faces can abut on one another when the threaded spindle is turned and that in this state of the expansion screw the central section of the threaded spindle provided with a tool attachment point is accessible from the outside.

U.S. Pat. No. 5,324,196 to Magill, teaches an orotracheal tube pacifier. The orotracheal tube pacifier includes an orotracheal tube, a pacifier portion for receiving the orotracheal tube, fastener means for holding securely the pacifier portion around the patient's head without the need for taping and the ultimate bruising, a face plate to which the fastener means and the pacifier portion are securely attached to, the face plate being relatively large as a safety precaution to hold the pacifier portion, a collet locking device fitting on the face plate and will not slipping or coming loose, and nipples affixed to the face plate and being designed to reduce the amount of palatal grooving.

U.S. Pat. No. 4,671,767 to Blechman, et al, teaches both fixed and removable functional appliances are disclosed employing magnets to provide the requisite force for accomplishing Class II malocclusion correction. Magnets are employed buccally and/or lingually, either operating in sliding or shearing mode or with the inter-pole gap inclined mesio-distally to develop an effective horizontal force component. Long thin rectangular magnets are incorporated bilaterally and inclined mesio-distally in the tooth capping sections of functional type base structures overlying the occlusal surface. Curved or angled straight magnets are located in anterior flanges of functional type base structures for developing horizontal thrust on the mandible. A number of closed magnetic circuits using either low reluctance keepers or shaped magnets are described for providing either increased force or travel or both.

U.S. Pat. No. 4,299,568, to Crowley, teaches a dual function orthodontic appliance which permits the orthodontist a wide variety of treatment options in repositioning the teeth to achieve the most orthodontically desirable positions and in maintaining the repositioned teeth in the desired positions. The orthodontic appliance of the present invention includes a palatal overlay molded to conform to the contours of the patient's hard plate and to fit securely against the gingival edge of the lingual surface of the teeth, a pair of posteriorly positioned opposed clasps, and a pair of opposed, spaced retaining and positioning wires which cross over the anterior teeth for a distance necessary to achieve the desired positioning or retaining effect. The orthodontic appliance of the present invention may be adapted to treat the lower teeth by providing in place of the palatal overlay a gingival overlay molded to conform to the periodontal structures on the lingual side of the lower teeth. An additional embodiment provided includes a single continuous substantially horizontal retaining wire having at least one preferably centrally positioned inverted U-shaped adjustment loop which may be clipped to convert the single wire appliance of this embodiment to the more versatile double wire configuration appliance.

U.S. Pat. No. 4,144,643, to Krygier, teaches a maxillary orthopedic suture separating orthodontic appliance which includes a pair of spaced anchor plates which are secured to bands on the teeth at opposite sides of the upper jaw and are connected together by offset adjusting means disposed for fitting in the palatal area.

U.S. Pat. No. 3,895,624 to Georgiade, teaches correction of maxillary and premaxillary deformities in infants with bilateral cleft lip and palate through the application of an intra-oral device capable of extra-oral activation. A miniature gear mechanism is provided for expansion of the maxillary segments and screw means for retraction of the premaillary segment. By positioning the premaillary segment in its appropriate relationship to the lateral maxillary segments, satisfactory repair of the bilateral cleft lip is accomplished in one stage.

U.S. Pat. No. 4,386,405 teaches to Lewin, et al, teaches a field generator, preferably a magnetic field generator, field flux pick-ups arranged at an interval therefrom, as well as an electronic device for the three-dimensional comprehension and evaluation of electrical signals arising in a field flux or a change of field flux. For displaying random points (P2 . . . Pn) of the lower jaw (1), means are provided which identify the geometrical attitude of the points with respect to a fixed-body coordinate system (xo, yo, Zo) allocated to the lower jaw whose origin and rotational center is the measuring point (P1). Further, a coordinate converter is provided which converts the coordinates (xo, yo, zo) related to the lower jaw into the coordinates (.DELTA.x2, .DELTA.y22 .DELTA.z2) of the stationary coordinate system (X, Y, Z). Further, summing amplifiers are provided which add the adjustment magnitudes (.DELTA.x2, .DELTA.y2, .DELTA.z2) of the jaw-related coordinates to the coordinates (x1, y1, z1) of the measuring point (P1). The device is particularly employed in gnathography.

U.S. Pat. No. 4,504,226 to Gordon, teaches axillary and mandibular arch models which are positioned in an articulator so that the plane of occlusion is in a three dimensional relationship about the articulator hinge axis substantially corresponding to the three dimensional relationship of the intraoral plane of occlusion about the mandibular hinge axis. A mechanically adjustable guide plane element is substituted in the place of one of the arch models and adjusted to fit the plane of occlusion of the other arch model. The teeth of such model are then adjusted in accordance with the occlusal plane guide. The occlusal plane guide is replaced by the heretofore removed arch model and its teeth are brought into centric relation occlusion with the previously adjusted arch model. The arch models are then discluded to a preselected centric wedge of opening of which an impression is made. A gnathological positioner may be fabricated from this impression.

U.S. Pat. No. 4,505,672 to Kurz, teaches a gnathologic orthodontic positioner which is split to provide an upper section for the maxillary arch and a separate lower section for the mandibular arch, the two sections being held together by elongated resilient members, such as elastics and/or by magnetic force. The upper and lower sections are attached to the teeth by mechanical clasps which may be assisted by suction cups.

U.S. Pat. No. 4,616,998 to Wong, teaches a novel face bow and method of its use for accurately transfering gnathological relationship data from a patient to an articulator. The face bow includes radioluscent arm pieces with radiopaque markers or indicators for locating critical points, the method of use comprising the mounting of the face bow on a patient in generally conventional fashion and then producing a cephalometric head x-ray of the patient with the improved face bow in place, the radioluscent arm pieces permitting anatomical features of the patient to be clearly viewed with precise correlation to reference planes. Radiopaque markers are located at various selected points on the face bow to accurately reflect the position of points of interest, such as an articulator's axis of rotation, such that these points become superimposed with the patient's anatomical features on the cephalometric head film.

U.S. Pat. No. 4,836,778 to Baumrind, et al, teaches a method and apparatus for monitoring, storing and displaying movements of a person's mandible in relation to the cranium, comprises a plurality of infrared LED's securely mounted to the cranium and to the jaw, in immovable relation to the mandible. The location of each LED, as determined by photodiodes as the LED's are sequentially turned on and of; is compared against an established three dimensional system frame of reference and through distinct local frames of reference associated with the cranium and the jaw, respectively, within the system frame of reference. A pointer, also provided with LED's is used to locate specific points on the mandible in reference to the movement described by the LED's attached to the lower jaw. The data is collected, calibrated and stored by a computer for subsequent display and analysis, either alone or in conjunction with a video display of the person's actual head and jaw as the data was taken.

U.S. Pat. No. 5,098,289 to Feher, teaches a model of the human head having a movable lower jaw is used in the analysis of gnathological relationships. The model receives reproductions of a dental patient's upper and lower dental arches and simulates the functional movements which occur during mastication and, in so doing, permits visual observation of the mandibular joints so that a course of therapy may be chosen.

U.S. Pat. No. 5,531,595 to Koutavas, teaches a method of determining the position of an upper jaw cast and a lower jaw cast using a dental articulator provides a disposable plastic holder in the lower jaw cast and mounts it in a metal bracket bar fitted to the base of the articulator whose telescoping post allows adjustment of the height of the head above the base. A bracket bar mounted on the head and spring biased so that this bracket bar can move in a plane and can pivot about a horizontal axis receives another plastic disposable holder which can fit into a cavity in the upper casting. Once the castings are properly positioned, a hard-enable composition can be cast into the recess to embed the holder in the upper casting.

U.S. Pat. No. 5,026,282 to Koike, teaches a physiological stereo articulator comprises a maxillary mechanism and a mandibular mechanism, and the lower frame member in the mandibular mechanism can turn about a center which is shifting while opening and closing as the human mandible does, and at the same time with the shifting of the center of turning, the vertical swinging of the lower frame member is caused. This construction permits simulation of the movement of the lower frame member to practical movement of the human mandible.

U.S. Pat. No. 5,502,087, to Tateosian, et al, teaches a dental prosthesis which includes polymeric material formed by heat curing a polymerizable composition having at least 5 percent by weight of at least one polymerizable Monomer having at least one acrylic moiety and a gram molecular weight of at least 200. The polymeric material is preferably formed by heat curing and has an unnotched Izod impact strength of at least 2.5 and more preferably at least 3.0 ft.lb/in as measured by a Modified ASTM D256, and a flexural fatigue life of at least 20,000 flexes to failure at 0.1 inch deflection. Preferably the polymerizable monomer has a vapor pressure less than 5 mm Hg at 23° C. A method of making a denture is provided which includes molding and polymerizing the polymerizable composition to form a denture. Preferably the polymerizable composition includes polymerizable compounds made up of at least 5 percent by weight of the acrylic Monomer having a gram molecular weight of at least 300 and less than 5 percent by weight of Volatile compounds and less than 2 percent by weight of Low Molecular Weight acrylic compounds having a gram molecular weight of less than 200.

U.S. Pat. No. 5,009,597, to Schaefer, teaches Composite dental prosthesis elements formed of filled acrylate- and/or methacrylate-based polymers and comprising a core having high flexural strength and a high bending modulus and an abrasion-resistant jacket with a highly lustrous surface are suitable for temporary and semipermanent as well as permanent installation with crowns and bridges, for inlays and the like.

The functional print of a prosthesis typically is designed to provide the precise contours of all the morphological structures of the patient's palate. Typically, when properly formed, both the convexity relief (or internal side) and the concave part (the part felt by the patient's tongue) of a palatal plate of the upper, partial or complete prosthesis, are produced as a smooth surface. Prior to the instant invention, the thickness of the prosthesis was a matter defined by the skill of the specific dental technician. Frequently in the past, a prosthesis of improper thickness caused phonetic flaws in the speech of a patient. The flaws were manifested in the form of uncontrolled hissing. It is hypothesized that this "hissing phenomenon" is caused when air circulates during pronunciation between the tongue and the smooth part of a partial or fill prosthesis having an improper thickness.

Mass production of so-called ready made prostheses has been met with only uncertain success in solving the hissing problem. Otherwise, custom fabrication by a skilled dental technician, although successful in most cases, is nonetheless expensive and time-intensive. It has been further observed that a substantial period of time is typically required for patients to become accustomed to such prior art prostheses. Thus, there exists a long felt need for a simple and inexpensive solution to the hissing problem.

SUMMARY OF THE INVENTION

The instant invention substantially solves the problems of the prior and fulfills a long felt need by providing a novel method and apparatus.

More specifically, the invention provides a method and apparatus for creating a prosthesis having a substantially uniformly predetermined thickness.

Still more specifically, the invention provides a method and apparatus for creating a prosthesis having a substantially uniformly predetermined thickness sufficient for substantially eliminating the hissing problem which would otherwise be manifested by the patient for whom it was created.

Still more specifically, the invention provides a method and apparatus for creating a prosthesis having a substantially uniformly predetermined thickness sufficient for substantially reducing the time which would otherwise be required for the patient to become accustomed to the prosthesis.

Here are the more important features of the invention as broadly outlined, in order that the detailed description that follows may be better understood; and in order for the present contribution to the art may be better appreciated. There are additional features of the invention that will be described hereinafter and which form the subject matter of the appended claims. Those of ordinary skill in the art will appreciate that the conception upon which this disclosure is based may readily be utilized as a basis for the designing of other structures, methods and systems for carrying out the several purposes of the instant invention. It is important, therefore, that the claims be regarded as including such equivalent constructions insofar as they do not depart from the spirit and scope of the instant invention.

Further, the purpose of the instant abstract is to enable the U.S. Patent and Trademark office and the public generally, and especially the scientists, engineers and practitioners in the art who are not familiar with patent or legal terms or phraseology, to determine quickly from a cursory inspection of it, the technical disclosure of the patent application. The abstract is neither intended to define the invention of the instant patent application, which is measured by the claims, nor is it intended in any manner to be limiting as to the scope of the instant invention.

In light of the foregoing, it is therefore an object of the instant invention to provide a new and improved method and apparatus which has all of the advantages of the prior art and none of its disadvantages.

It is another object of the instant invention to provide a new and improved apparatus which may be easily and efficiently manufactured and marketed.

It is another object of the instant invention to provide a new and improved apparatus which is of a durable and reliable construction.

It is another object of the instant invention to provide a new and improved apparatus which can be manufactured at low cost with regard to both labor and materials, and which accordingly can be sold at a correspondingly lower cost, thus promoting commerce.

It is a further object of the instant invention to provide a new and improved method and apparatus which provides at least some of the advantages of the prior art schemes, while simultaneously eliminating at least some of the disadvantages of them.

It is a further object of the instant invention to provide a new and improved method and apparatus which are particularly designed for solving the hissing problem otherwise experienced by a patient whose palatal prosthesis does not have a uniform predetermined thickness.

It is a further object of the instant invention to provide an apparatus which does not required a skilled technician to operate and thus, can be used as a low cost method of creating a palatal prothesis having a uniform predetermined thickness.

It is a further object of the instant invention to provide an apparatus which does not required a skilled technician to operate and thus, can be used as a low cost method of creating a palatal prothesis having a uniform predetermined thickness sufficient for eliminating the hissing problem which could otherwise be manifested without intervention of the instant method and apparatus.

It is a further object of the instant invention to provide an apparatus which does not required a skilled technician to operate and thus, can be used as a low cost method of creating a palatal prothesis having a uniform predetermined thickness sufficient for substantially reducing the time period otherwise required for a patient to become accustomed to the prosthesis.

Other objects, features, and advantages of the instant invention, in its details of construction and arrangement of parts, will be seen from the above, from the following description of the preferred embodiment when considered in light of the drawings and the appended claims.

BRIEF DESCRIPTION OF THE DRAWINGS

FIG. 2a shows an elevation view of the shaft and shaft elevator assembly.

FIG. 2b shows a cutaway elevation view of the shaft and shaft elevator assembly rotated 90° about its longitudinal axis relative to FIG. 2a.

FIG. 3 shows a cutaway elevation view of the base of the instant apparatus.

FIG. 4 shows a cutaway elevation view of the lower mold affixed to the lower mold support.

FIG. 5 shows an elevation view of the entire apparatus with a cutaway section of the upper and lower molds directly after the formation of the upper mold.

FIG. 6 shows an elevation view of the entire apparatus with a cutaway section of the upper and lower molds after the upper and lower molds have been separated by a distance of "A."

DETAILED DESCRIPTION OF THE DRAWINGS

Figures 1, 1A:
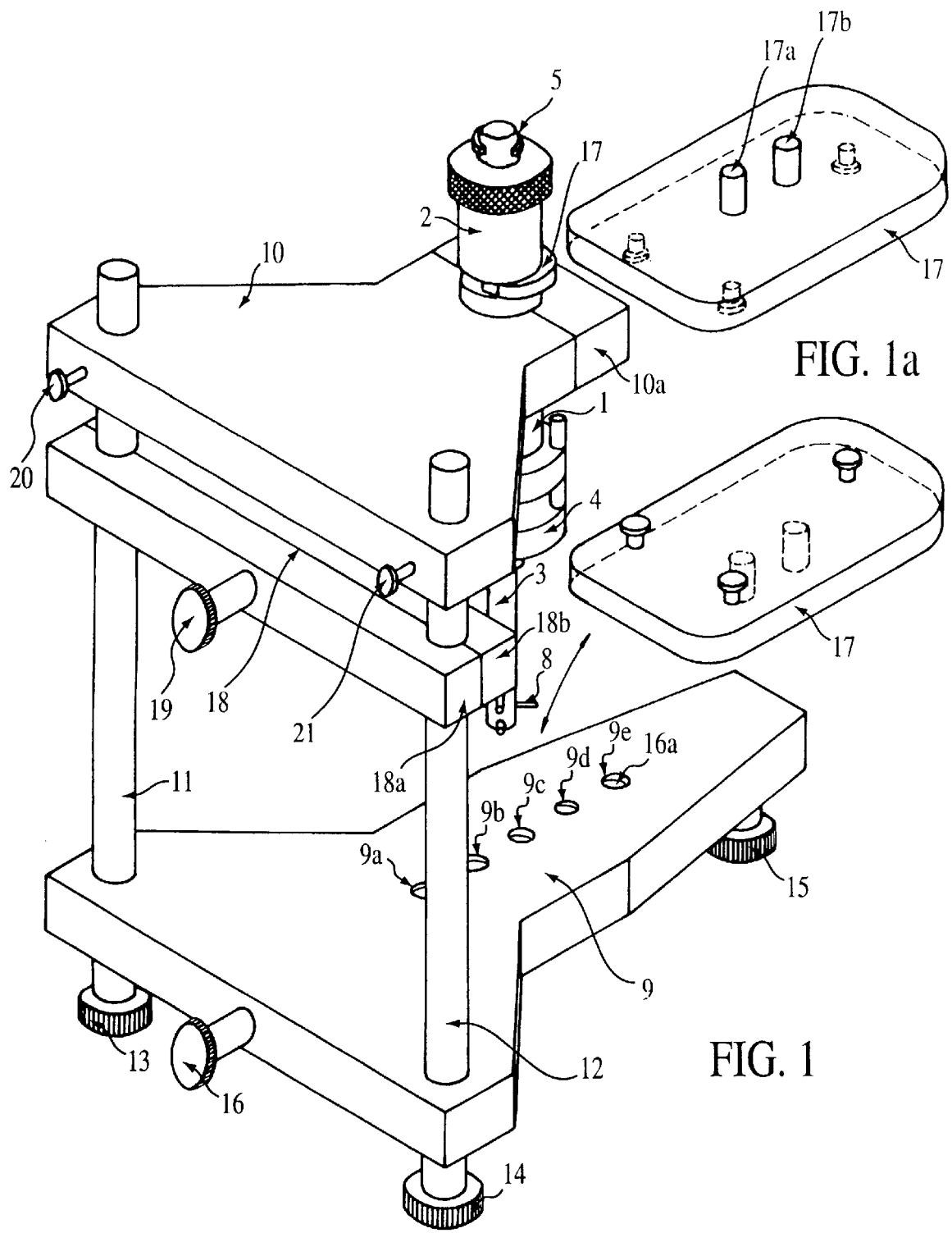
FIG. 1 shows an isometric view of the apparatus of the instant invention in its entirety with all the elements, showing an exploded view of the lower casting support.
FIG. 1a shows an exploded view of the bottom surface of the lower casting support of the invention.

FIG. 1 shows an isometric view of the apparatus of the invention in its entirety. The major components of the apparatus of the invention include: a base 9 with leveling posts 13–15; and lower casting support holes 9a–c. Also illustrated is shaft elevator assembly support 10 and its tightening screws 20, 21; support posts 11, 12; shaft elevator support stopper 18 and its tightening screw 19; shaft elevator assembly which includes: shaft elevator 2; cylinder 1; shaft crown 4 and shaft 3 including lower casting retention elements 8. Also shown is an exploded partial phantom view of lower casting support 17. Also depicted is the lower casting support 17, including lower casting base retension fixing elements 17a, b, depicted in phantom view. The apparatus is shown in its elevated shaft mode wherein shaft 3 has been elevated relative to base 9 by a distance equal to the thickness of thickness measuring element 7.

FIG. 1a, shows the flip side of the view of the lower casting support shown in FIG. 1, also depicting the three casting retension elements in phantom view.

FIG. 2a shows a partial elevation of the apparatus of the invention which depicts only the shaft elevator assembly, including: shaft elevator 2, further including middle outer screw threaded portion 2d; knurled shaft elevator rotating collar 2b; shaft 3; shaft crown 4, including shaft crown posts 4a; and, cylinder 1, including cylinder base 4b, further including notches for force fit fixing cylinder base 4b against shaft crown posts 4a.

FIG. 2b shows a cutaway partial elevation view of the shaft elevator assembly, rotated 90° about its longitudinal axis, relative to FIG. 2a. Shaft elevator 2 includes knurled collar 2a; screw threads 1a at its outer mid portion; and, retainer 5 for vertically fixing shaft 3 to shaft elevator 2. It is the only element depicted in FIG. 2b which is designed to be rotated about the central longitudinal axis of the assembly. All other elements depicted in FIG. 2b are not rotatable about the longitudinal axis of the assembly. The figure also depicts shaft 3, which includes at the lowest, end thereof upper casting retention elements 8. Further shown is shaft crown 4 which includes shaft crown base 4b and shaft crown posts 4a. Shaft crown 4 is fixed to shaft 3 by set screw 6. Still further shown is cylinder 1 which includes a screw threaded inner surface 2d at its upper most end, for engaging the screw threads 1a of shaft elevator 2; and cylinder base 1b, which includes notches for engaging crown posts 4a in a force fit relationship sufficient to substantially fix cylinder 1 to shaft crown 4. The cylinder 1 is more particularly depicted in its cutaway elevation view in FIG. 2b. Still more particularly shown are screw threads 1a positioned on the lower end outer surface of elevator 2.

FIG. 3 shows a partial cutaway elevation of view of base 9, which particularly depicts openings 9a–e, into which lower casting support retention elements 17a, b, are inserted and fixed to base 9 by a setscrew 16. Also depicted are leveling posts 13 and 15.

FIG. 4 shows a partial cutaway elevation view of the lower casting support 17, further including a base layer of plaster 23 upon which plaster model 22. Model 22 includes a true convex contour impression of the patient's palate on its upper surface which is formed by following conventional procedures of the prior art.

FIG. 5 shows an elevation view of the entire apparatus with a cutaway view of the upper and lower castings after formation of the upper casting 24 on top of lower casting 22. Upper casting 24 is prepared by preferably coating the surface of lower casing 22 with a conventional release material such as a silicone oil or the like, and pouring the casing material over the substantially entire upper surface of the lower casting to a depth sufficient to securely engage the casting retentions elements 8 of shaft 3. After the casting material of the upper casting has sufficiently set, the upper casting 24 is vertically displaced from lower casting 22 in the manner depicted if FIG. 6.

FIG. 6 shows an elevation view of the entire apparatus with a cutaway view of the upper and lower castings after the upper casting 24 is vertically displaced (but not angularly displaced) from lower casting 22, by rotating knurled collar 2b (see FIG. 2a) through a distance "A;" and at the same time, shaft elevator 2 is vertically displaced from cylinder 1 by a distance "A," as measured thickness measuring element 7. The space between the thusly displaced upper casting 24 and lower casting 22 is thereafter filled with a suitable molding material to form the final prototype of the palatal prosthesis of the instant invention. The space between the upper and lower moldings can be set at a distance "A" and filled with a liquid plastic. Alternatively the upper molding can be raised more than a distance "A" and a pliable soft sheet of a suitable molding material can be inserted between the upper and lower moldings. The shaft 3 can thereafter be lowered by turning knurled collar 2b until the distance between the upper and lower castings is reduced to a distance "A."

The thickness of the thickness of the palatal prosthesis so produced is determined by the technicians's choice of the thickness measuring element 7. A thickness from about 0.1 mm to about 10.0 mm is typical; a thickness from about 0.3 mm to about 7.0 mm is preferred; and a thickness from 0.5 mm to about 3.0 mm is most preferred.

The prosthesis of the instant invention can be made from any material known to the prior art. Typical of such materials include, but are not necessarily limited to, plastics such as those disclosed in the above cited U.S. Pat. Nos. 5,502,087 and 5,009,597, incorporated herein by reference. Other preferred materials of construction include plastics selected from the group of polyethylene, polyvinylidene fluoride, poly(methyl methacrylate), polystyrene, nylon, polyethylene terephthalate, poly(tetramethylene terephthalate), polyetheresters of poly(tetramethylenie terephthalate), polyetheretherketone, wax, hard wax, and combinations thereof.

The term "patient" [and its variants], as used herein, refer to that person for whose use the prosthesis of the instant invention was designed.

The terms "mold" and "casting" [and their variants] as used herein are meant to be equivalent and interchangeable.

Although the invention has been described with reference to certain preferred embodiments, it will be appreciated that many variations and modifications may be made within the scope of the broad principles of the invention. Hence, it is intended that the preferred embodiments and all of such variations and modifications be included within the scope and spirit of the invention, as defined by the following claims.

I claim:

1. A method for forming a palatal plate prosthesis of a substantially precise, predetermined uniform thickness, comprising:
   providing an apparatus for forming said palate prosthesis, which includes a first element for fixing a first casting which includes a first impression of the palate of a patient; wherein said first impression is fixed by said first component, so as to generally lie in a first horizontal plane; a second component for fixing a second casting which includes a second impression formed by applying casting material over the substanial entirety of said first impression; wherein said second impression is movably fixed by said second component, so as to generally lie in a second horizontal plane which is generally parallel and equidistant from said first horizontal plane; and, a third component for enabling vertical displacement of said first impression from said second impression substantially precisely equal to said predetermined uniform thickness;
   providing said first casting fixed on said first component;
   providing said second casting fixed on said second component;
   manipulating said third component sufficient to cause a vertical displacement between said first impression and said second impression, substantially precisely equal to said predetermined uniform thickness; and,
   forming said palatal plate prosthesis within said vertical displacement.

2. The method of claim 1, wherein said vertical displacement is selected from a range of about from 0.5 to 3.0 mm.

3. The method of claim 2, wherein the material of construction of said palatal plate prosthesis is selected from the group of consisting of polyethylene, polyvinylidene fluoride, poly(methyl methacrylate), polystyrene, nylon, polyethylene terephthalate, poly(tetramethylene terephthalate), polyetheresters of poly(tetramethylene terephthalate), polyetheretherketone, wax, hard wax, and combinations thereof.

4. The method of claim 3, wherein said first impression is concave and said second impression is convex.

5. The method of claim 3, wherein said first impression is convex and said second impression is concave.

6. An apparatus for forming a palatal plate prosthesis of a substantially precise, predetermined uniform thickness, comprising:
   a base having three leveling supports;
   a first component attachable to said base in one of a plurality of positions, for fixing a first casting which includes a first impression of the palate of a patient; wherein said first impression is fixed by said first component, so as to generally lie in a first horizontal plane;
   a second component for fixing a second casting which includes a second impression formed by applying casting material over the substantial entirety of said first impression; wherein said second impression is movably fixed by said second component, so as to generally lie in a second horizontal plane which is generally parallel to, and equidistant from, said first horizontal plane; and,
   a third component for enabling vertical displacement of said first impression from said second impression substantially precisely equal to said predetermined uniform thickness; wherein said third component farther includes:
      a shaft having at least one retention element at the lowest end thereof, for fixing said second casting thereto; and,
      a shaft elevator for vertically, non-rotationally, displacing said shaft;
   a fourth component attached to said shaft elevator for supporting said third component;
   a stop located between said shaft elevator and said fourth component for stopping downward vertical travel of said shaft elevator;
   a spacer having a thickness substantially equal to said substantially precise, predetermined uniform thickness, insertable between the lowest outermost end of said shaft elevator and said stop;
   at least one generally vertical post for fixing said fourth component to said base; and,
   wherein said base further comprises more than two openings, each spaced apart sufficient to enable said lower casting support to be fixed to said base at, at least more than one position, and a single set screw for substantially fixing said lower casting support at said position.

7. An apparatus for forming a palatal plate prosthesis of a substantially precise, predetermined uniform thickness, comprising:
   a first component for fixing a first casting which includes a first impression of the palate of a patient; wherein said first impression is fixed by said first component, so as to generally lie in a first horizontal plane;

a second component for fixing a second casting which includes a second impression formed by applying casting material over the substantial entirety of said first impression; wherein said second impression is movably fixed by said second component, so as to generally lie in a second horizontal plane which is generally parallel to, and equidistant from, said first horizontal plane; and, a third component for enabling vertical displacement of said first impression from said second impression substantially precisely equal to said predetermined uniform thickness, including a spacer having a thickness substantially equal to said substantially precise, predetermined uniform thickness, insertable between the lowest outermost end of said shaft elevator and said stop.

* * * * *